(12) United States Patent
Hata et al.

(10) Patent No.: US 10,357,347 B2
(45) Date of Patent: Jul. 23, 2019

(54) ELECTRIC TOOTHBRUSH

(71) Applicants: Colgate-Palmolive Company, New York, NY (US); Omron Healthcare Co., Ltd., Kyoto (JP)

(72) Inventors: Yasunori Hata, Kyoto (JP); Tadashi Tone, Kyoto (JP); Hideaki Yoshida, Kyoto (JP)

(73) Assignee: Colgate-Palmolive Company, New York, NY (US)

( * ) Notice: Subject to any disclaimer, the term of this patent is extended or adjusted under 35 U.S.C. 154(b) by 9 days.

(21) Appl. No.: 15/552,687

(22) PCT Filed: Feb. 24, 2016

(86) PCT No.: PCT/US2016/019332
§ 371 (c)(1),
(2) Date: Aug. 22, 2017

(87) PCT Pub. No.: WO2016/138115
PCT Pub. Date: Sep. 1, 2016

(65) Prior Publication Data
US 2018/0014923 A1 Jan. 18, 2018

(30) Foreign Application Priority Data
Feb. 25, 2015 (JP) ................................ 2015-035752

(51) Int. Cl.
*A61C 17/22* (2006.01)
*A61C 17/34* (2006.01)

(52) U.S. Cl.
CPC ........ *A61C 17/3481* (2013.01); *A61C 17/221* (2013.01); *A61C 17/222* (2013.01); *A61C 17/224* (2013.01)

(58) Field of Classification Search
CPC ................................ A61C 17/22; A61C 17/34
USPC .......................................................... 15/22.1
See application file for complete search history.

(56) References Cited

U.S. PATENT DOCUMENTS

2015/0020325 A1\* 1/2015 Yoshida ............... A61C 17/222
15/22.1

FOREIGN PATENT DOCUMENTS

WO WO2011/086960 7/2011

OTHER PUBLICATIONS

International Search Report and the Written Opinion of the International Searching Authority issued in International Application PCT/US2016/019332 dated May 19, 2016.

\* cited by examiner

*Primary Examiner* — Michael D Jennings (57) ABSTRACT

An electric toothbrush includes a stem member on which a replaceable toothbrush is mounted. The stem member is made of synthetic resin and has a cavity for accommodating a DC motor and a vibration shaft connected to the DC motor. One end of the cavity is opened for inserting the DC motor and the vibration shaft together, and the other end thereof is closed. A free end of the vibration shaft is rotatably supported at the closed end of the cavity. The cavity has a cone-shaped wall so that the DC motor is firmly held in the cavity by a rigid contact between a shoulder portion of the DC motor and the cone-shaped wall.

23 Claims, 8 Drawing Sheets

ELECTRIC TOOTHBRUSH

BACKGROUND

Electric or powered toothbrushes that are currently available in the market have a number of constructing parts. Such parts are, for example: a body for holding a battery and an electric circuit board; a DC motor; an eccentric shaft connected to the DC motor; and a stem for holding the eccentric shaft and the DC motor. In the motor receiving cavity, detent protrusions are provided for securing the DC motor within the cavity. However, because the stem is typically formed from a synthetic resin, it is difficult to form the cavity through a single injection molding process. Also, the vibration of the eccentric shaft is transmitted through the motor and the stem to the bristle rather than directly to the stem, which results in a reduction in power and the production of excessive noise. Furthermore, the motor is located close to the tooth cleaning elements, which requires a small sized motor and results in low vibration power. Finally, the weight balance of the existing electric toothbrushes is difficult to adjust because the location of the motor is limited. Thus, a need exists for an electric toothbrush that addresses the above-noted issues in the existing devices of this type.

BRIEF SUMMARY

The present invention may be directed, in one aspect, to an electric toothbrush including a stem member on which a replaceable toothbrush is mounted. The stem member is made of synthetic resin and has a cavity for accommodating a DC motor and a vibration shaft connected to the DC motor. One end of the cavity is opened for inserting the DC motor and the vibration shaft together, and the other end thereof is closed. A free end of the vibration shaft is rotatably supported at the closed end of the cavity. The cavity has a cone-shaped wall so that the DC motor is firmly held in the cavity by a rigid contact between a shoulder portion of the DC motor and the cone-shaped wall.

In one aspect, the invention may be an electric toothbrush comprising: an elongated body portion having a cylindrical room which accommodates a battery and an electric circuit board, said elongated body portion having a first end and a second end; a stem member made of a synthetic resin and having an elongated cavity with a closed end and an open end, in which the open end of the stem member is connected to the first end of the elongated body portion, said elongated cavity having a cone-shaped wall extending from the open end towards the closed end of the elongated cavity such that the size of the opening of the cone-shaped wall close to the open end is wide and is gradually narrowed towards a middle point of the elongated cavity which is located between the closed end and the open end, said elongated cavity further having a recessed hole formed at the closed end such that an axis of the recessed hole is in alignment with an axis of the cone-shaped wall; a replaceable brush-brush mounted on the stem member; a DC motor inserted in the elongated cavity from the open end and firmly held in the elongated cavity by a rigid contact between a shoulder portion and/or side surface of the DC motor and the cone-shaped wall; and a vibration shaft having one end connected to the DC motor and another end formed with an axial shaft portion which is rotatably inserted into the recessed hole, said vibration shaft having an eccentric shaft whose gravity center is located at a position deviated from an axis of the DC motor, wherein a first distance between the gravity center of the eccentric shaft and the axial shaft portion is less than a second distance between the shoulder portion of the DC motor and the gravity center.

In another aspect, the invention may be an electric toothbrush comprising: an elongated body portion having an interior cavity which accommodates a battery and an electric circuit board, said elongated body portion having a first end and a second end; a stem member configured to receive a replaceable brush removeably mounted thereon, the stem member having an elongated cavity with a closed end and an open end, the open end being connected to the first end of the elongated body portion, said elongated cavity defined by an interior wall at least a portion of which tapers from the open end towards the closed end, said elongated cavity further having a recessed hole formed at the closed end; a vibration shaft having an end formed with an axial shaft portion which is rotatably inserted into the recessed hole at a first contact point, said vibration shaft having an eccentric shaft with a gravity center; a DC motor disposed at least partially in the elongated cavity and connected to another end of the vibration shaft opposite the axial shaft portion, wherein a shoulder portion and/or a side surface of the DC motor contacts the interior wall of the elongated cavity at a second contact point, wherein the gravity center of the eccentric shaft is offset from an axis of the DC motor; and wherein a first distance between a gravity center of the eccentric shaft and the first contact point is less than a second distance between the gravity center and the second contact point.

In yet another aspect, the invention may be an electric toothbrush comprising: an elongated body portion having an interior cavity which accommodates a battery and an electric circuit board; a stem member having an elongated cavity with a closed end and an open end, the open end being adjacent to the elongated body portion, said elongated cavity having a cone-shaped wall extending from the open end towards the closed end of the elongated cavity such that a cross-sectional area of the elongated cavity gradually decreases from the open end towards a middle point of the elongated cavity which is located between the closed end and the open end, said elongated cavity further having a recessed hole formed at the closed end, wherein the stem member is configured to receive a replaceable brush removeably mounted thereon; a DC motor positioned in the elongated cavity and such that a shoulder portion and/or a side surface of the DC motor is in contact with the cone-shaped wall; and a vibration shaft having one end connected to the DC motor and another end formed with an axial shaft portion which is rotatably inserted into the recessed hole, said vibration shaft having an eccentric shaft with a gravity center, wherein a first distance between the gravity center of the eccentric shaft and the axial shaft portion is less than a second distance between the shoulder portion of the DC motor and the gravity center.

According to a preferred embodiment, the vibration shaft comprises an extension shaft and the eccentric shaft which are connected in alignment with each other such that the extension shaft is located between the DC motor and the eccentric shaft.

According to a preferred embodiment, the cone-shaped wall is formed by a wall surrounding all around the DC motor.

According to a preferred embodiment, the cone-shaped wall is formed by a plurality of ribs forming wall segments surrounding intermittently around the DC motor.

According to a preferred embodiment, an upper portion of the elongated body portion is bent with respect to a lower portion thereof.

According to a preferred embodiment, said elongated cavity has a receiving corner at a narrowed end of the cone-shaped wall.

According to a preferred embodiment, a third distance between the first end of the elongated body portion and the should portion of the DC motor is less than the second distance.

According to a preferred embodiment, the cone-shaped wall is formed by a curved wall which is curved from the open end towards the closed end.

According to a preferred embodiment, the cone-shaped wall is formed by an upright wall portion and a slanted wall portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 1:
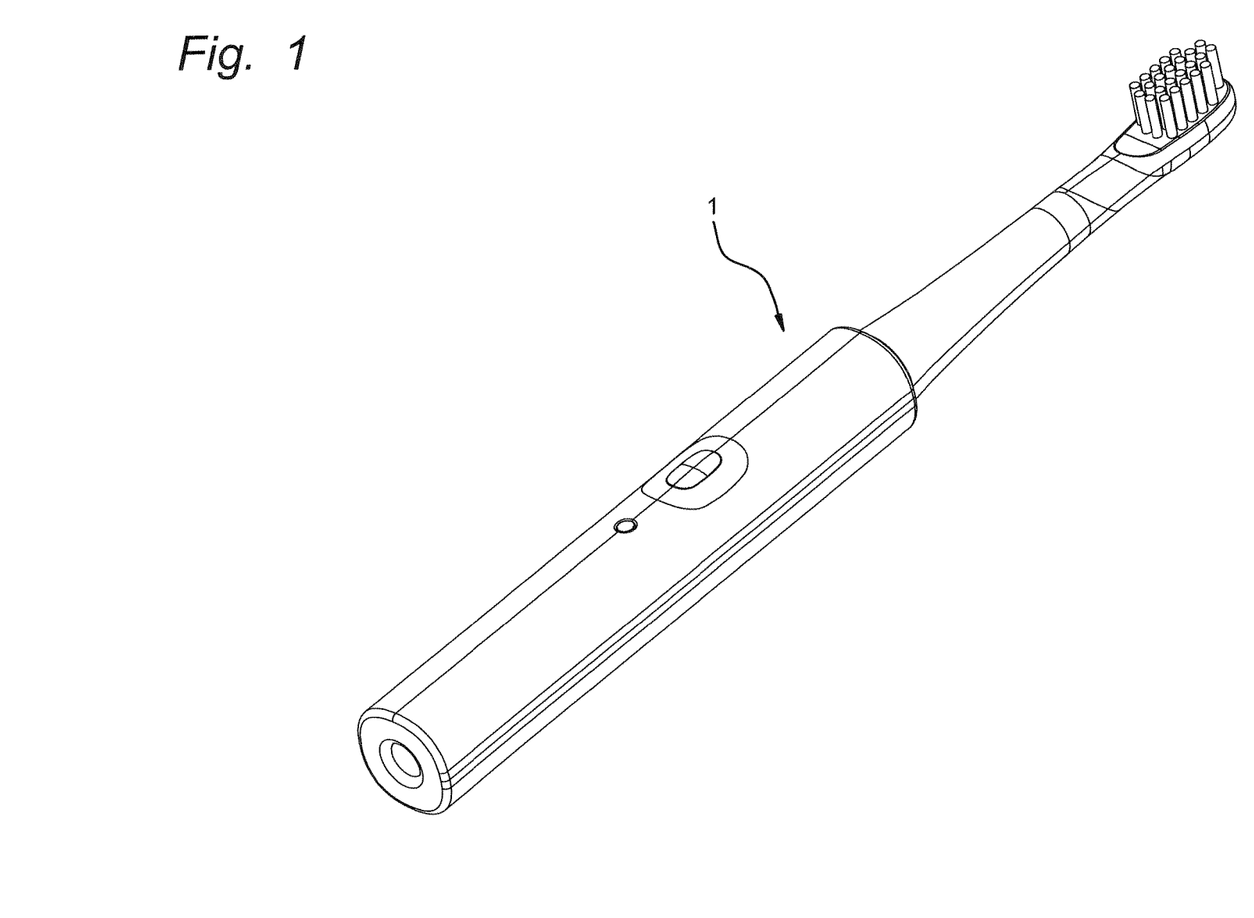
FIG. 1 is a perspective view of an electric toothbrush according to a preferred embodiment of the present invention.

Referring to FIG. 1, an electric toothbrush 1 according to a preferred embodiment of the present invention is shown.

Figure 2A:
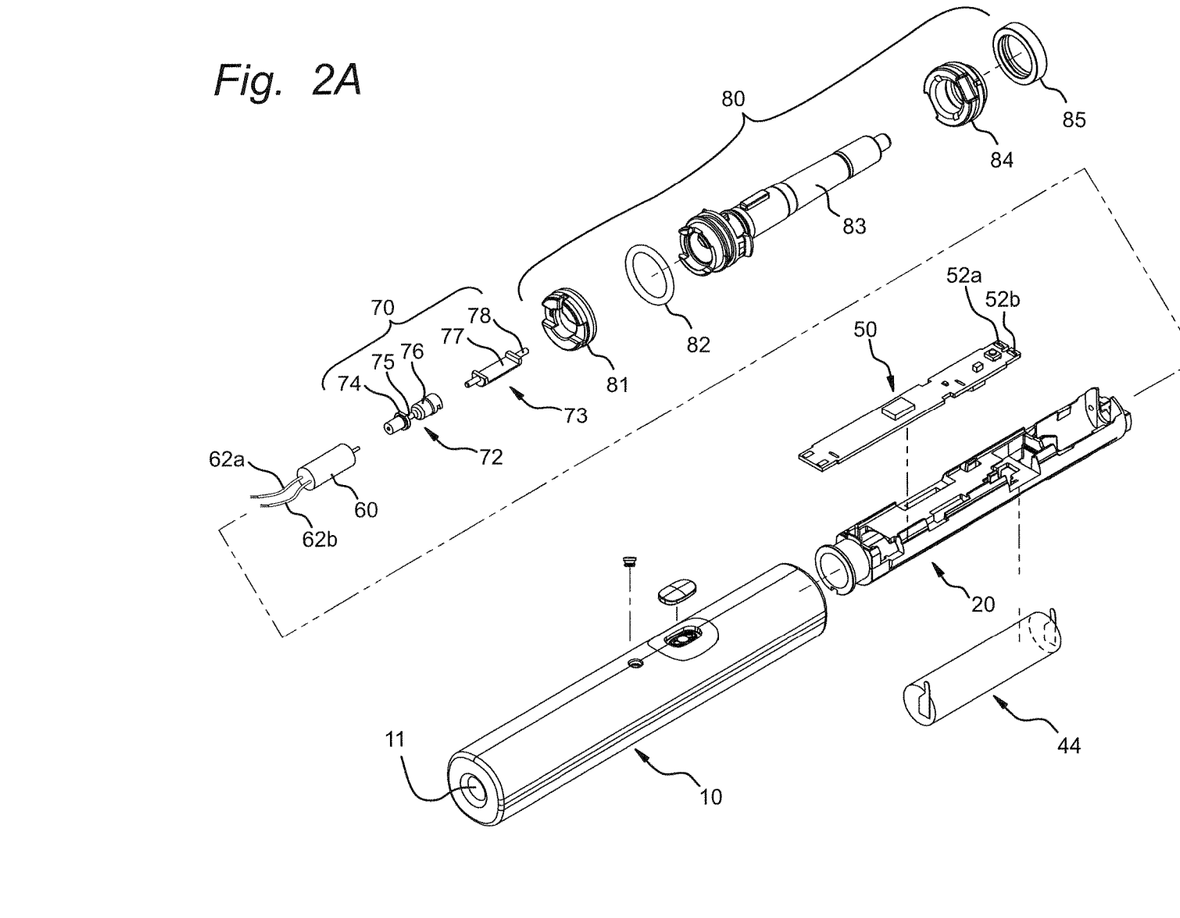
FIG. 2A is an exploded view of the electric toothbrush shown in FIG. 1.

Referring to FIG. 2A, an exploded view of the electric toothbrush 1 is shown. Electric toothbrush 1 includes an elongated body portion 10, a chassis 20, a rechargeable battery 44, an elongated circuit board 50, a DC motor 60 having a cylindrical body, a vibration shaft 70 and a stem arrangement 80. A replaceable brush (not shown) is to be mounted on the stem arrangement 80. The replaceable brush covers the stem arrangement 80 completely or partially.

The body portion 10 is capable of being gripped or grasped by a user and has a recess 11 at its bottom end for receiving therein a projection of a battery charger. The body portion 10 has an interior cavity, which may be for example, cylindrical, for accommodating the chassis 20, the rechargeable battery 44, and circuit board 50.

The stem arrangement 80 includes a bottom support member 81, a packing ring 82, a stem member 83, a top support member 84 and a top ring 85. The stem member 83 has an elongated cavity 86 for receiving the vibration shaft 70 and the DC motor 60.

Figure 2B:
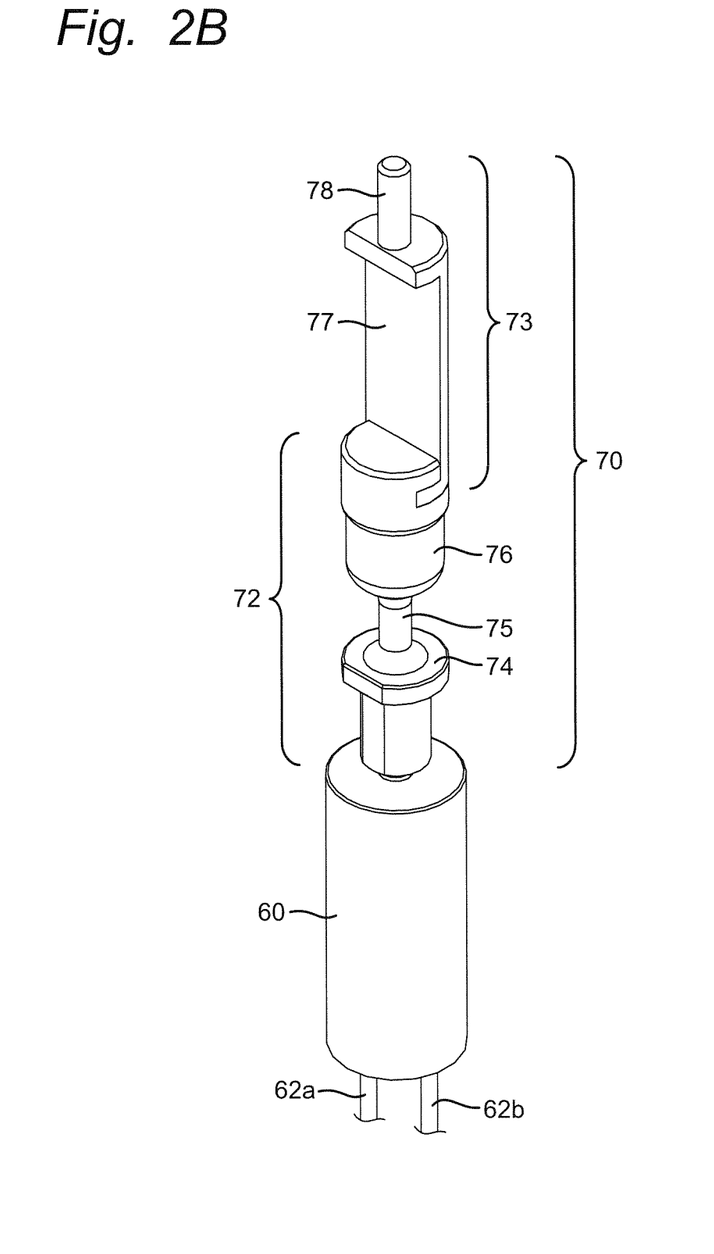
FIG. 2B is a perspective view of a vibration shaft shown in FIG. 2A.

Referring to FIG. 2B, the vibration shaft 70 includes an extension shaft 72 made of synthetic resin and an eccentric shaft 73 made of metal. The extension shaft 72 may be integrally formed by a material called POM (polyoxymethylene) manufactured by, for example, POLYPLASTICS CO., LTD. JAPAN. The grade of the material POM may be NW-02 or grades, such as M90-44.

As shown in FIG. 2B, the extension shaft 72 of the vibration shaft 70 includes a collar portion 74 provided close to a bottom end, a resilient shaft portion 75 and a connecting portion 76 which are integrally formed by POM in the exemplified embodiment. The bottom end face of the extension shaft 72 is formed with a recess to be engaged with a shaft of the DC motor 60. DC motor 60 has two wires 62a and 62b extending from a bottom face thereof for electric connection with the circuit board 50.

The eccentric shaft 73 of the vibration shaft 70 includes an eccentric portion 77 and an axial shaft portion 78. The bottom end of the eccentric portion 77 is firmly connected to the connecting portion 76 by molding and the upper end of the eccentric portion 77 is provided with the axial shaft portion 78.

When the vibration shaft 70 rotates about its axis by the DC motor 60, the eccentric portion 77 generates a high frequency vibration which is transmitted to the stem arrangement 80 and to the brush (not shown). The resilient shaft portion 75 has a flexibility to receive the high frequency vibration of the eccentric portion 77.

Figure 2C:
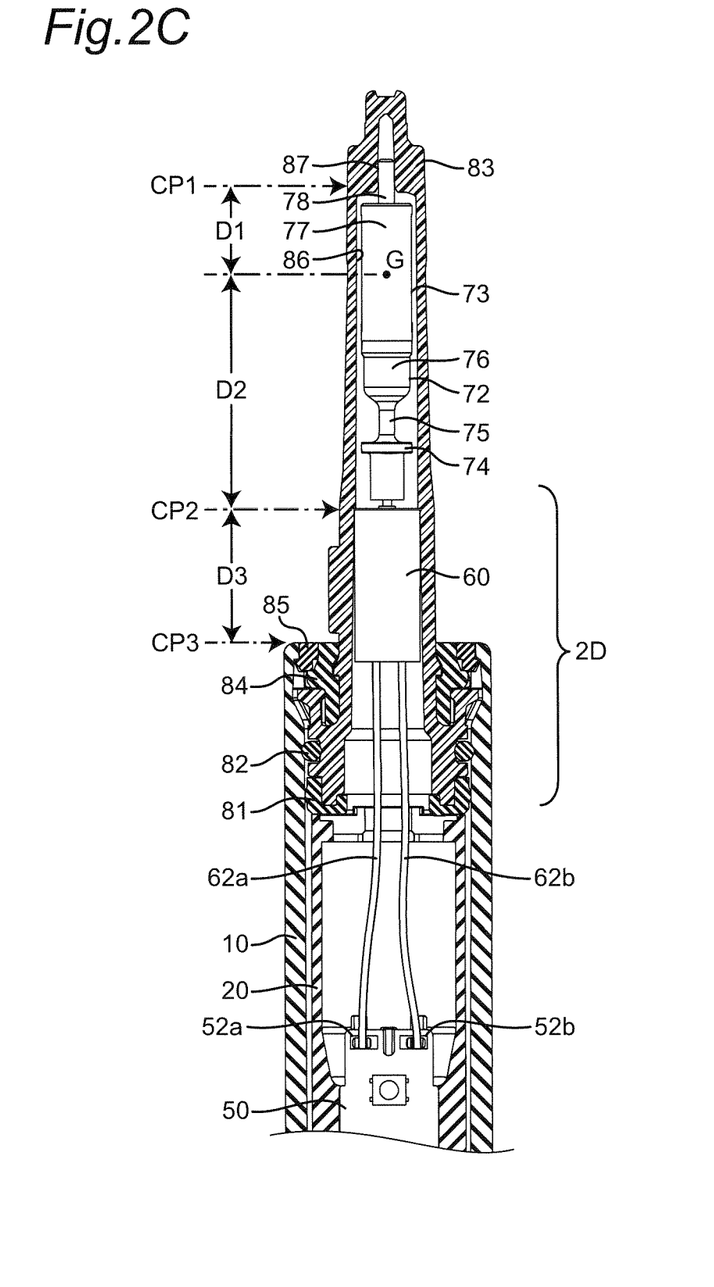
FIG. 2C is a cross-sectional view of a stem member inserted with the vibration shaft and the DC motor.

Referring to FIG. 2C, the stem member 83 may also be formed by POM. A recessed hole 87 is formed at the end of the elongated cavity 86. The recessed hole 87 slidably receives the axial shaft portion 78. The elongated cavity 86 accommodates therein the vibration shaft 70 and the DC motor 60. The vibration shaft 70 is freely rotated in the elongated cavity 86. The recessed hole 87 serves as a bearing for freely holding the axial shaft portion 78. The vibration shaft 70 freely rotates inside the elongated cavity 86 even under high frequency vibration.

Since the recessed hole 87 serves as the bearing, it is not necessary to provide a separate bearing arrangement for rotatably holding the axial shaft portion 78.

Figure 2D:
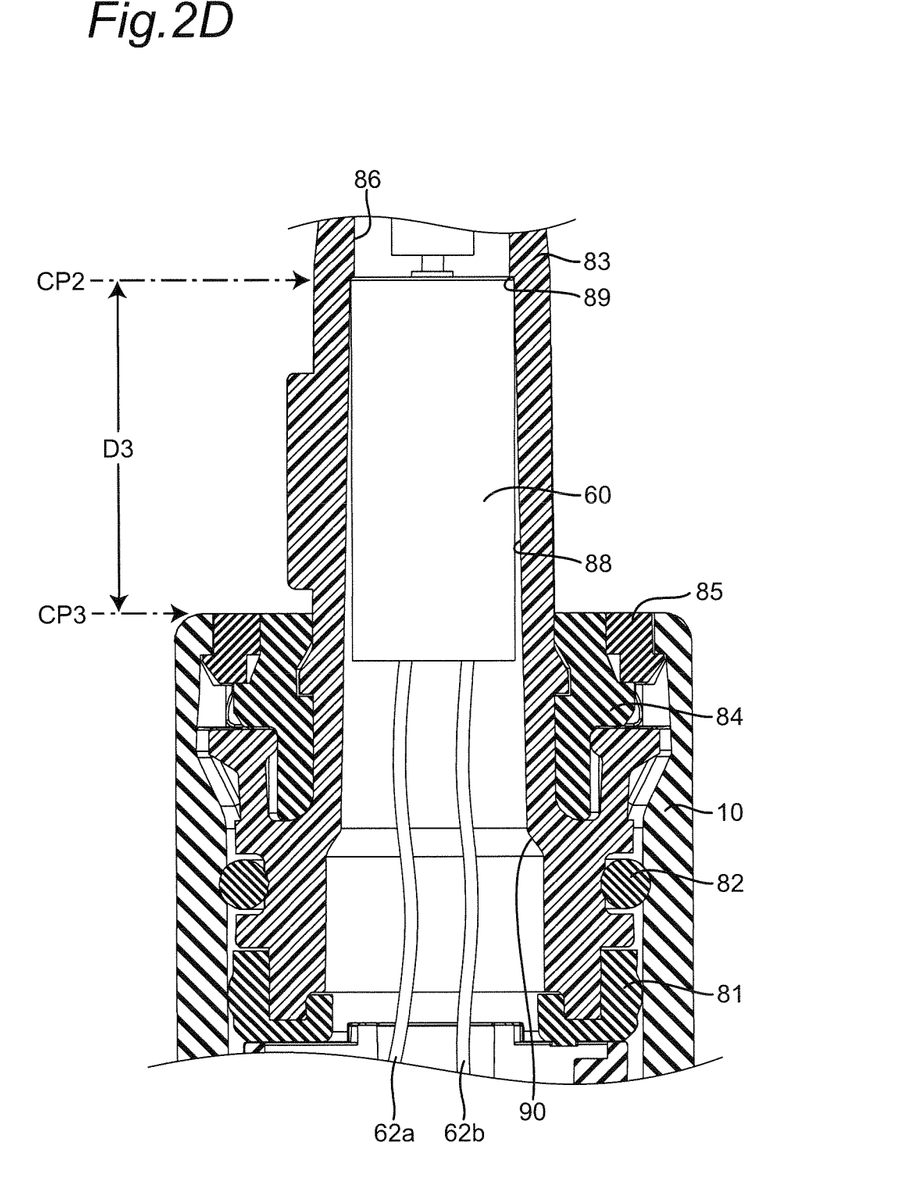
FIG. 2D is an enlarged cross-section view of a portion 2D shown in FIG. 2C.

A portion 2D indicated in FIG. 2C is shown in an enlarged scale in FIG. 2D.

Referring to FIG. 2D, a lower end portion of the stem member 83 is shown in detail. The elongated cavity 86 has an open end at the lower end of the stem member 83 so that the two wires 62a and 62b of DC motor 60 extends through the open end of the elongated cavity and through an opening formed in the chassis 20, and terminates at electrodes 52a and 52b formed on the circuit board 50, as shown in FIG. 2C.

Referring back to FIG. 2D, the elongated cavity 86 has a cone-shaped wall 88 and a receiving corner 89 at the end of the cone-shaped wall 88. The cone-shaped wall 88 is widest at the open end of the elongated cavity 86, and is gradually narrowed towards a middle point of the elongated cavity, such as at the receiving corner 89. The inner diameter of the cone-shaped wall 88 at the receiving corner 89 is about the same or slightly smaller than the outer diameter of the DC motor 60. The inner diameter of the cone-shaped wall 88 at the open end of the elongated cavity 86 is between 105% and 145% of, such as for example but not limited to 132% of, the outer diameter of the DC motor 60. The cone-shaped wall 88 is formed with a wall surrounding all around the DC motor 60 without any intermittence. Also, the cone-shaped wall is straight from the open end to the receiving corner 89. According to a variation, the cone-shaped wall 88 may have a step portion or a slanted step portion 90 at which the inner diameter of the cylindrical cavity 86 is widened abruptly.

The DC motor 60 together with the vibration shaft 70 is inserted into the elongated cavity 86 from the open end, and forcibly pushed in until the upper side edge, i.e., a shoulder portion, of the DC motor 60 is fittingly held at the end of the cone-shaped wall 88 such that the shoulder portion and/or side surface, such as upper side surface, of the DC motor 60 makes a rigid contact with the cone-shaped wall. The top surface of the DC motor 60 may abut against the receiving corner 89. If necessary, a bonding agent may be applied between the shoulder portion and the cone-shaped wall, or between the top surface of the DC motor 60 and the receiving corner 89. When the shoulder portion and/or side surface of the DC motor 60 is firmly held in the cone-shaped wall 88, the axial shaft portion 78 is slidably inserted into the recessed hole 87. It is apparent from the above that an axis of the recessed hole 87 is in alignment with an axis of the cone-shaped wall 88.

As shown in FIG. 2C, a vibration generator defined by the DC motor 60 and vibration shaft 70 is positioned inside the stem member 83 such that the axial direction of the DC motor 60 is in alignment with the axial direction of the vibration shaft 70, and that the vibration generator is held in the elongated cavity 86 at two contact points CP1 and CP2. Contact point CP1 is a point anywhere in the axial shaft portion 78 and, more specifically, a point where the axial shaft portion 78 contacts the recessed hole 87, and contact point CP2 is at a point where the shoulder portion of the DC motor 60 contacts the cone-shaped wall 88.

A distance D1 between contact point CP1 and a gravity center G of eccentric shaft 73 is smaller than a distance D2 between contact point CP2 and the gravity center G of eccentric shaft 73 (D1<D2). This arrangement enables the location of the eccentric shaft 73 to be relatively close to the contact point CP1, i.e., close to a position where the bristle of the toothbrush is located. Thus, the vibration generated by the eccentric shaft 73 can be effectively transmitted through axial shaft portion 78 and recessed hole 87 to the bristle of the toothbrush. According to a preferred embodiment of the invention, distance D2 is 10 mm or greater, such as 21.3 mm. Furthermore, DC motor 60 is located within a lower side of the stem member 83, i.e., a side of a lower half-length (a side away from the bristle of the toothbrush) of full length of the stem member 83. This arrangement provides an appropriate weight balance of the stem member 83 loaded with the vibration generator, and eventually an appropriate weight balance of the electric toothbrush 1. Also, this arrangement gives a freedom to select a larger size of DC motor 60, in comparison to a case where the DC motor is located in a side of an upper-half length of full length of the stem member 83. In order to provide a sufficient distance between eccentric shaft 73 and DC motor 60, the extension shaft 72 is provided. In a modification, it is possible to connect DC motor 60 directly to the eccentric shaft 73 without using any extension shaft 72.

Furthermore, the elongated cavity 86 is widest at the open end and is gradually narrowed towards the receiving corner 89 and thereafter the diameter is narrowed at the receiving corner 89 and keeps a constant width or further narrowed towards the closed end until reaching the recessed hole 87. Thus, the molding of the stem member 83 with the elongated cavity 86 gradually narrowed towards the closed end can be easily formed by an injection molding.

Furthermore, DC motor 60 can be held in a position without using any screws, but only by a single push and the resulting friction fit. Accordingly, the assembly of the stem member 83 loaded with the vibration generator is simple and can be done very easily.

Referring again to FIG. 2A, after placing the rechargeable battery 44 and the circuit board 50 at proper positions in the chassis 20, the ends of the two wires 62a and 62b are soldered to electrodes 52a and 52b, respectively, of the circuit board 50. Then, the chassis 20 carrying the battery 44 and circuit board 50 is inserted into the body portion 10. During the insertion, stem member 83 is also partly inserted into the body portion 10 together with the bottom support member 81, packing ring 82, top support member 84 and top ring 85, as shown in FIG. 2C. Accordingly the stem member 83 and the body portion 10 are firmly held together in a watertight manner.

It is to be noted that stem member 83 and body portion 10 can be formed integrally. In this case a bottom end of the body portion 10 where the recess 11 is formed should be opened to allow the insertion of an assembly of the vibration shaft 70, DC motor 60, and chassis 20 mounted with battery 44 and circuit board 50. After the assembly is inserted from the bottom open end, the open end should be tightly closed by a cap member.

Referring to FIG. 2D, the most top position of the contact point between the body portion 10 and the stem member 83 is a contact point CP3. In other words, contact point CP3 corresponds to an upper end of the elongated body portion 10. According to a preferred embodiment, DC motor 60 intersects with a level of the contact point CP3. In other words, the length of DC motor 60 is longer than a distance D3 between contact points CP2 and CP3. In some arrangements, it is possible to make the length of DC motor 60 shorter than a distance between contact points CP2 and CP3. Furthermore the distances are so selected that D3 is less than D2 (D3<D2), as apparent from FIG. 2C. This arrangement has an advantage of producing an appropriate vibration of the stem member 83.

Figure 3A:
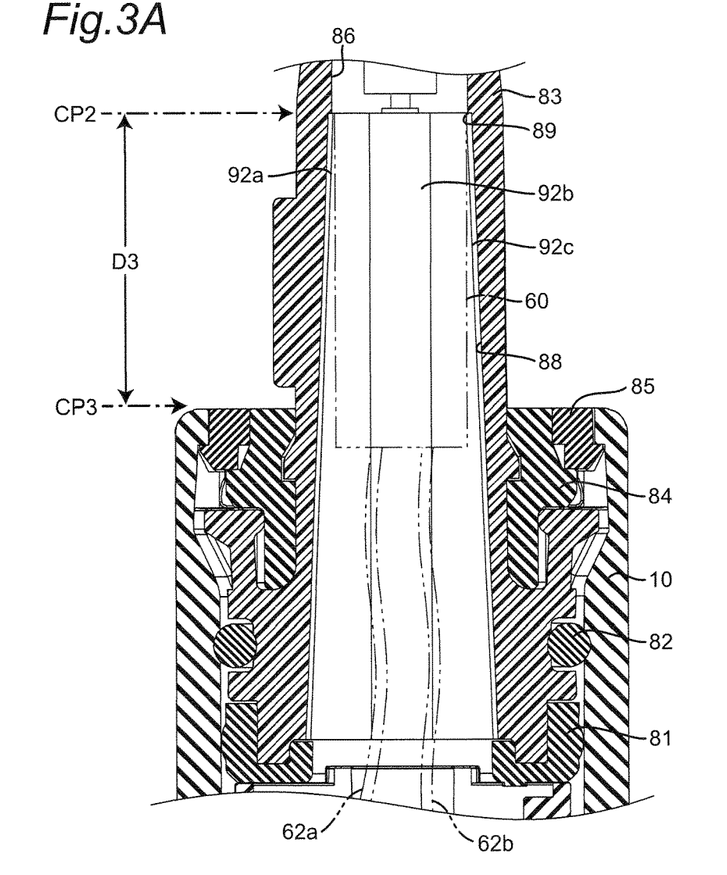
FIG. 3A is view similar to FIG. 2D, but particularly showing a first modification of a cone-shaped wall formed in a stem member.
Figure 3B:
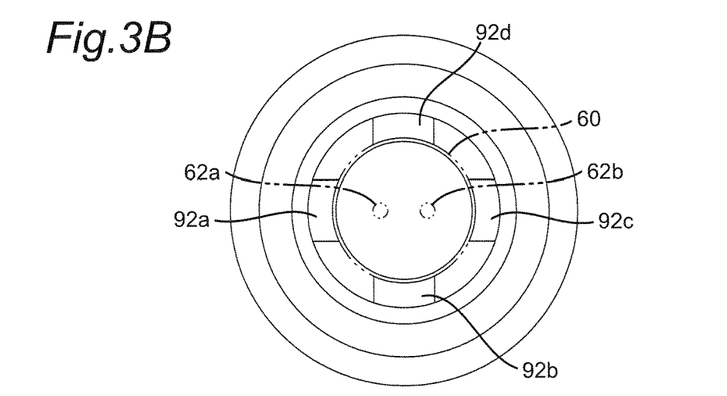
FIG. 3B is a bottom view of the stem member shown in FIG. 3A.

Referring to FIGS. 3A and 3B, a first modification of the cone-shaped wall is shown. The cone-shaped wall is defined by a plurality of, such as four ribs 92a, 92b, 92c and 92d, located in the cylindrical cavity 86 extending parallel to each other from the receiving corner 89 to the open end of the elongated cavity 86. The four ribs 92a, 92b, 92c and 92d are spaced equidistantly from each other along the circumference of the open end of the elongated cavity 86. The free end surfaces of the four ribs define wall segments surrounding intermittently around the DC motor, as best shown in FIG. 3B.

The number of ribs can be two or greater. Also, the ribs may extend from the receiving corner 89 to an intermediate place somewhere between the receiving corner 89 to the open end of the elongated cavity 86, such as to the slanted step portion 90 (see FIG. 2D).

Figure 3C:
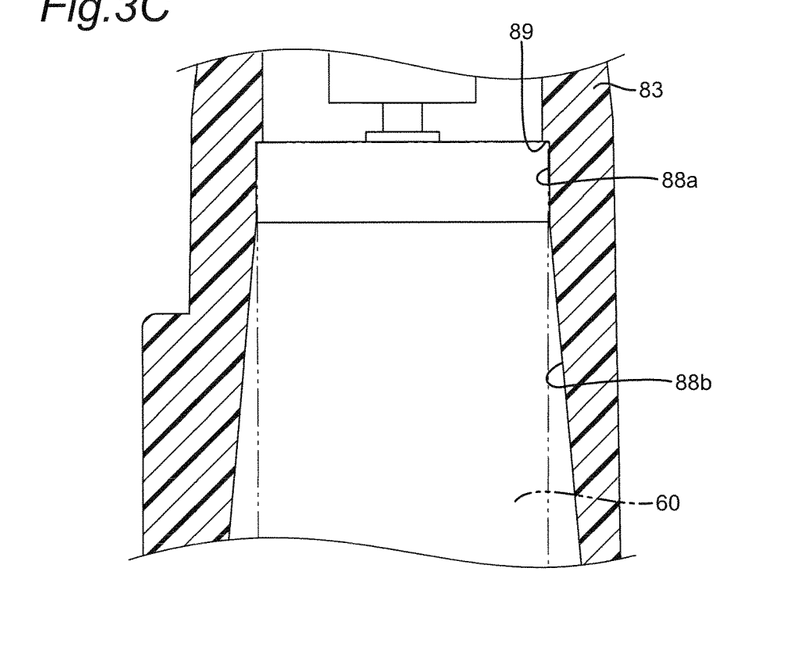
FIG. 3C is an enlarged view, and particularly showing a second modification of a cone-shaped wall formed in a stem member.

Referring to FIG. 3C, a second modification of the cone-shaped wall is shown. The cone-shaped wall 88 is formed by an upright wall portion (88a), and a slanted wall portion 88b. At upright wall portion 88a, the inner diameter of the wall is constant, i.e., nearly equal to the diameter of the DC motor 60. At slanted wall portion 88b, the inner diameter of the wall increases from the end of the upright wall portion 88a towards the open end of the elongated cavity 86.

Figure 3D:
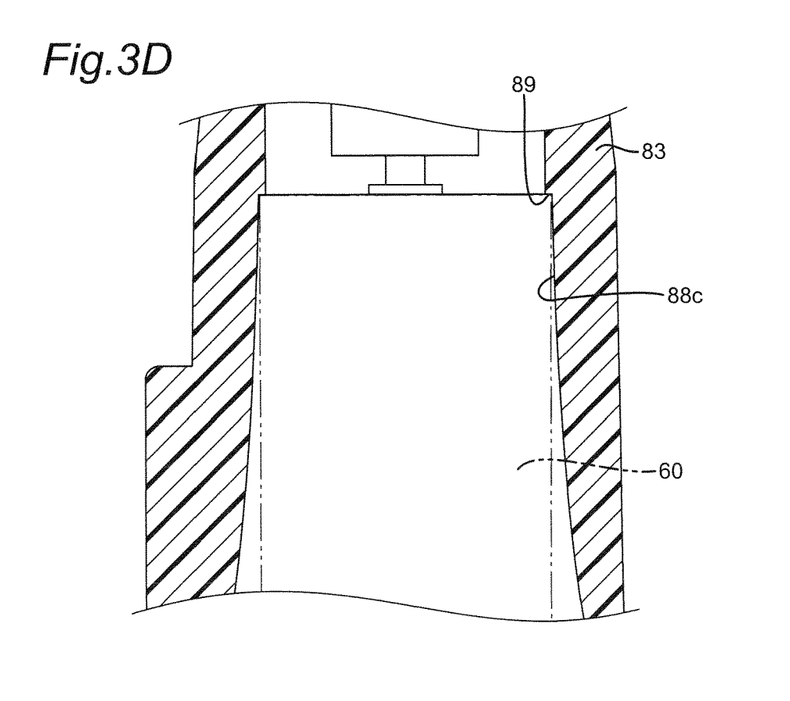
FIG. 3D is an enlarged view, and particularly showing a third modification of a cone-shaped wall formed in a stem member.

Referring to FIG. 3D, a third modification of the cone-shaped wall is shown. The cone-shaped wall 88c is curved from the open end to the closed end. Preferably, the curvature becomes great towards the open end.

Figure 4:
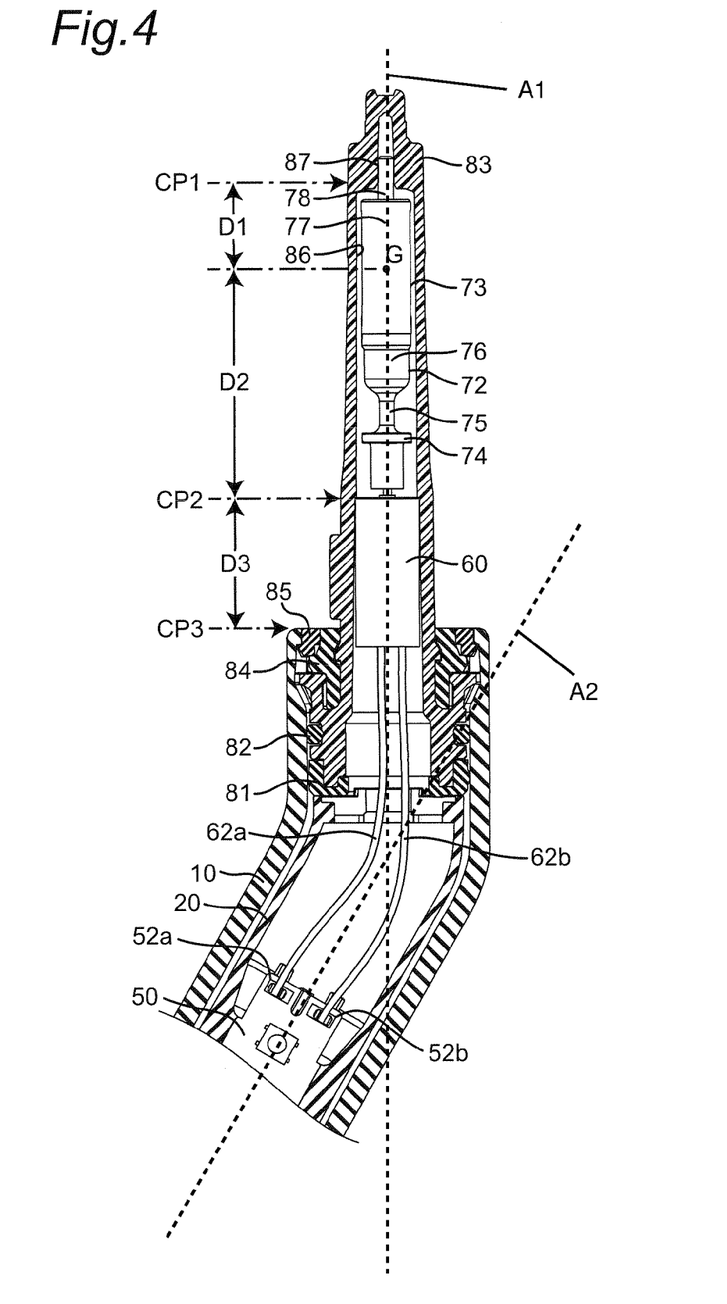
FIG. 4 is a view similar to FIG. 2C, but particularly showing a modification of an elongated body portion.

Referring to FIG. 4, a modification of the body portion 10 is shown which is bent at neck portion thereof. The body portion 10 has an upper portion bent with respect to a lower portion thereof. Therefore, an axis A1 of the upper portion of body portion 10 is inclined with respect to an axis A2 of the lower portion thereof. Even in such an arrangement, since the DC motor 60 is not located in the body portion 10, but in the stem member 83, it is not necessary to provide any flexible shaft that is bent between the DC motor 60 and the eccentric shaft 73. Therefore, a freedom of designing the body portion 10 is increased.

Furthermore, according to one embodiment of the present invention, the DC motor 60 which is described as having a cylindrical body can be arranged to have a cone-shaped body such that the wide side of the cone-shaped body is located close to the open end of the elongated cavity 86 and the narrow side of the cone-shaped body is located close to the closed end of the elongated cavity 86. In this case, the outer wall of the cone-shaped body is more upright, i.e., less inclined with respect to the axis of the DC motor, than the cone shaped wall 88.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An electric toothbrush comprising:
   an elongated body portion (10) having an interior cavity which accommodates a battery (44) and an electric circuit board (50);
   a stem member (83) having an elongated cavity (86) with a closed end and an open end, the open end being adjacent to the elongated body portion (10), said elongated cavity (86) having a cone-shaped wall (88) extending from the open end towards the closed end of the elongated cavity (86) such that a cross-sectional area of the elongated cavity (86) gradually decreases from the open end towards a middle point of the elongated cavity (86) which is located between the closed end and the open end, said elongated cavity (86) further having a recessed hole (87) formed at the closed end, wherein the stem member (83) is configured to receive a replaceable brush removeably mounted thereon;
   a DC motor (60) positioned in the elongated cavity (86) such that a shoulder portion or a side surface of the DC motor (60) is in contact with the cone-shaped wall (88); and
   a vibration shaft (70) having one end connected to the DC motor (60) and another end formed with an axial shaft portion (78) which is rotatably inserted into the recessed hole (87), said vibration shaft (70) having an eccentric shaft (73) with a gravity center (G),
   wherein a first distance (D1) between the gravity center (G) of the eccentric shaft (73) and the axial shaft portion (78) is less than a second distance (D2) between the shoulder portion of the DC motor (60) and the gravity center (G).

2. The electric toothbrush according to claim 1, wherein the vibration shaft (70) comprises an extension shaft (72) and the eccentric shaft (73) which are connected in alignment with each other such that the extension shaft (72) is located between the DC motor (60) and the eccentric shaft (73).

3. The electric toothbrush according to claim 1, wherein the cone-shaped wall (88) circumferentially surrounds the DC motor (60) along an entirety of a length of the DC motor (60).

4. The electric toothbrush according to claim 1, wherein the cone-shaped wall (88) is formed by a plurality of ribs (92a, 92b, 92c, 92d) forming wall segments surrounding intermittently around the DC motor (60).

5. The electric toothbrush according claim 1, wherein an upper portion of the elongated body portion (10) is bent with respect to a lower portion thereof.

6. The electric toothbrush according to claim 1, wherein said elongated cavity (86) has a receiving corner (89) at a narrowed end of the cone-shaped wall (88).

7. The electric toothbrush according to claim 6 wherein a top surface of the DC motor (60) is in surface contact with the receiving corner (89).

8. The electric toothbrush according to claim 6 wherein an inner diameter of the cone-shaped wall (88) at the receiving corner (89) is the same or slightly smaller than a maximum outer diameter of the DC motor (60).

9. The electric toothbrush according to claim 8 wherein the inner diameter of the cone-shaped wall (88) at the open end of the elongated cavity (86) is between 105% and 145% of the maximum outer diameter of the DC motor (60).

10. The electric toothbrush according to claim 1 wherein at least a portion of the side surface of the DC motor (60) is spaced apart from the cone-shaped wall (88).

11. The electric toothbrush according to claim 1, wherein a third distance (D3) between a first end of the elongated body portion (10) from which the stem member (83) extends and the shoulder portion of the DC motor (60) is less than the second distance (D2).

12. The electric toothbrush according to claim 1, wherein the cone-shaped wall (88) is formed by a curved wall which is curved from the open end towards the closed end.

13. The electric toothbrush according to claim 1, wherein the cone-shaped wall (88) is formed by an upright wall portion (88a) and a slanted wall portion (88b).

14. The electric toothbrush according to claim 1, wherein the DC motor (60) has a cylindrical body.

15. The electric toothbrush according to claim 1, wherein the DC motor (60) has a cone-shaped body.

16. The electric toothbrush according to claim 1 wherein an axis of the recessed hole (87) is aligned with an axis of the cone-shaped wall (88).

17. The electric toothbrush according to claim 1 wherein the stem member (83) has a length and is divided into a lower-half portion and an upper-half portion each extending for half of the length of the stem member (83), and wherein the DC motor (60) is located entirely within the lower-half portion of the stem member (83).

18. The electric toothbrush according to claim 1 wherein the elongated body portion (10) extends from a first end to a second end, the stem member (83) extending from the first end, and wherein a portion of the motor (60) extends to below the first end of the elongated body portion (10).

19. The electric toothbrush according to claim 18 wherein the first end of the elongated body portion (10) lies along a plane that intersects the motor (60).

20. An electric toothbrush comprising:
an elongated body portion (10) having an interior cavity which accommodates a battery (44) and an electric circuit board (50), said elongated body portion (10) having a first end and a second end;
a stem member (83) configured to receive a replaceable brush removeably mounted thereon, the stem member (83) having an elongated cavity (86) with a closed end and an open end, the open end being connected to the first end of the elongated body portion (10), said elongated cavity (86) defined by an interior wall (88) at least a portion of which tapers from the open end towards the closed end, said elongated cavity (86) further having a recessed hole (87) formed at the closed end;
a vibration shaft (70) having an end formed with an axial shaft portion (78) which is positioned within the recessed hole (87) at a first contact point (CP1) in the recessed hole (87) proximate the open end of the elongated cavity (86), said vibration shaft (70) having an eccentric shaft (73) with a gravity center (G);
a DC motor (60) disposed at least partially in the elongated cavity (86) and connected to another end of the vibration shaft (70) opposite the axial shaft portion (78), wherein a shoulder portion or a side surface of the DC motor (60) contacts the interior wall (88) of the elongated cavity (86) at a second contact point (CP2) proximate the closed end of the elongated cavity (86); and
wherein a first distance (D1) between the gravity center (G) of the eccentric shaft (73) and the first contact point (CP1) is less than a second distance (D2) between the gravity center (G) and the second contact point (CP2).

21. The electric toothbrush according to claim 20 wherein the gravity center (G) of the eccentric shaft (73) is offset from an axis of the DC motor (60).

22. The electric toothbrush according to claim 20, wherein said elongated cavity (86) has a receiving corner (89) at a narrowed end of the interior wall (88), and wherein a top surface of the DC motor (60) is in surface contact with the receiving corner (89).

23. The electric toothbrush according to claim 22 wherein an inner diameter of the interior wall (88) at the receiving corner (89) is the same or slightly smaller than a diameter of the portion of the DC motor (60) that is located at the receiving corner (89).

* * * * *